(12) United States Patent
Caserta et al.

(10) Patent No.: US 7,780,094 B2
(45) Date of Patent: Aug. 24, 2010

(54) VEHICLE AIR FRESHENER DIFFUSER

(75) Inventors: Andrea Caserta, Cerdanyola Del Valles (ES); Ruben Garcia Fabrega, Cerdanyola Del Valles (ES); Xavier Alvarez Leal, Cerdanyola Del Valles (ES)

(73) Assignee: Zobele Espana, S.A., Barcelona (ES)

( * ) Notice: Subject to any disclaimer, the term of this patent is extended or adjusted under 35 U.S.C. 154(b) by 0 days.

(21) Appl. No.: 10/490,901

(22) PCT Filed: Sep. 18, 2003

(86) PCT No.: PCT/ES03/00467

§ 371 (c)(1), (2), (4) Date: Jun. 13, 2006

(87) PCT Pub. No.: WO2004/091673

PCT Pub. Date: Oct. 28, 2004

(65) Prior Publication Data

US 2007/0001025 A1 Jan. 4, 2007

(30) Foreign Application Priority Data

Apr. 16, 2003 (WO) ............... PCT/ES03/00179

(51) Int. Cl.
- *A24F 25/00* (2006.01)
- *B05B 15/00* (2006.01)
- *B05B 9/00* (2006.01)
- *A62B 7/08* (2006.01)
- *F24F 6/00* (2006.01)

(52) U.S. Cl. .................. 239/34; 239/44; 239/47; 239/49; 239/51.5; 239/55; 239/57; 239/58; 239/59; 239/289; 239/326; 422/124; 454/337

(58) Field of Classification Search ............ 239/34, 239/44, 51.5, 55, 59, 58, 6, 289, 326, 57, 239/47, 49; 422/124; 454/337
See application file for complete search history.

(56) References Cited

U.S. PATENT DOCUMENTS 1,831,654 A * 11/1931 Cross ................ 239/34

(Continued)

FOREIGN PATENT DOCUMENTS

EP 1 031 446 A1 8/2000

(Continued)

*Primary Examiner*—Len Tran
*Assistant Examiner*—Steven M Cernoch
(74) *Attorney, Agent, or Firm*—Schiff Hardin LLP

(57) ABSTRACT

A diffuser for an air freshener product includes a casing having front and rear casing portions fastened together. A neck opening is formed inside said casing into which a neck of an air freshener reservoir is secured. A wick extends from the neck of the air freshener reservoir into the interior of the casing. The casing has openings in the front and back through which air flows. An air flow control element is provided in the casing to permit a user to change the air flow to the wick and thereby vary the air freshener product dispersed into the air. The air flow control element has a knob extending from the casing that is operable by the user. The rear portion of the casing has a fastener to which is attached a clip having two extended flexible arms that engage into a vent grill of an air conditioner system of a vehicle. The clip is securable in the fastener at positions oriented 90 degrees from one another to enable the clip to be fastened to vertically or horizontally oriented air conditioner grill slats.

15 Claims, 12 Drawing Sheets

U.S. PATENT DOCUMENTS

| | | | |
|---|---|---|---|
| 2,555,047 A * | 5/1951 | Logue | 239/58 |
| 3,617,035 A * | 11/1971 | Hoeher | 261/99 |
| 3,754,707 A * | 8/1973 | Morane | 239/59 |
| 3,970,219 A * | 7/1976 | Spitzer et al. | 222/1 |
| 4,154,398 A | 5/1979 | Gualandi | |
| 4,258,874 A * | 3/1981 | Webinger et al. | 229/120 |
| 4,293,095 A * | 10/1981 | Hamilton et al. | 239/35 |
| 4,306,679 A * | 12/1981 | Dusek et al. | 239/59 |
| 4,502,630 A * | 3/1985 | Haworth et al. | 239/34 |
| 4,523,870 A * | 6/1985 | Spector | 454/157 |
| 4,545,917 A * | 10/1985 | Smith et al. | 510/224 |
| 4,549,693 A * | 10/1985 | Barlics | 239/58 |
| 4,621,768 A | 11/1986 | Lhoste et al. | |
| 4,759,501 A * | 7/1988 | Silvenis et al. | 239/6 |
| 4,948,453 A * | 8/1990 | Nobile et al. | 156/441.5 |
| 5,324,490 A * | 6/1994 | Van Vlahakis et al. | 422/305 |
| 5,388,714 A * | 2/1995 | Zutler | 220/4.24 |
| 5,520,617 A * | 5/1996 | Wei | 601/134 |
| 5,521,357 A * | 5/1996 | Lock et al. | 219/543 |
| 5,527,493 A * | 6/1996 | McElfresh et al. | 261/30 |
| 5,603,455 A * | 2/1997 | Lin | 239/44 |
| 5,820,792 A * | 10/1998 | Lin | 261/30 |
| 5,903,710 A * | 5/1999 | Wefler et al. | 392/392 |
| 5,932,147 A * | 8/1999 | Chen | 261/30 |
| 5,988,520 A * | 11/1999 | Bitner | 239/6 |
| 6,050,551 A * | 4/2000 | Anderson | 261/30 |
| 6,103,201 A * | 8/2000 | Green | 422/124 |
| 6,264,887 B1 * | 7/2001 | Farmer | 422/5 |
| 6,374,044 B1 * | 4/2002 | Freidel | 392/390 |
| 6,502,762 B2 * | 1/2003 | Tuttobene, Jr. | 239/59 |
| 6,655,604 B2 * | 12/2003 | Tuttobene, Jr. | 239/6 |
| 6,976,637 B2 * | 12/2005 | Massimo | 239/44 |
| 7,140,553 B2 * | 11/2006 | Zobele | 239/34 |
| 2002/0179746 A1 * | 12/2002 | Reed | 239/569 |
| 2003/0066901 A1 * | 4/2003 | Tuttobene, Jr. | 239/6 |
| 2006/0202050 A1 * | 9/2006 | Caserta et al. | 239/34 |

FOREIGN PATENT DOCUMENTS

| | | |
|---|---|---|
| EP | 1 195 277 A1 | 4/2002 |
| ES | 0 283 811 U | 9/1986 |
| ES | 1 050 062 U | 2/2002 |

* cited by examiner

US 7,780,094 B2

VEHICLE AIR FRESHENER DIFFUSER

BACKGROUND OF THE INVENTION

1. Field of the Invention

The present invention relates generally to a diffuser of air-freshening or aromatic products, and in particular to an air-freshening product diffuser for use inside a motor vehicle, and in a preferred embodiment to a diffuser having a structure by which the diffuser is fastening to a diffuser grill of the air conditioning system of the vehicle.

2. Description of the Related Art

Diffusers are known from historical times which use a small recipient container of the air-freshening product, in the form of a bottle, from the mouth of which projects a wick through which ascends the air-freshening product by capillary action. The air which is circulating comes into contact with the projecting section of the wick and causes a rapid evaporation of the product and its consequent passage into the atmosphere. Also known from historical times is the controlling of the flow of air through the wick in some manner, to thereby control the delivery level of the product into the atmosphere.

As mentioned in U.S. Pat. No. 4,621,768, in which the portion of a wick projecting from the flask or reservoir is surrounded by and extends through a cylindrical neck that is fitted with wide side vents for the passage of air. A screw thread for axial displacement of a cap is provided coaxially facing the wick, so that when the cap undergoes a rotational movement an axial displacement of the cap takes place by acting on the casing of the diffuser. The axial movement permits a blocking to a greater or lesser extent, and even full blocking, of the vents of in the cylindrical neck, regulating the circulation of air through the vents.

It is also known, through the European patent document EP 1 031 446, that when the diffuser is intended to be located inside an automobile, it is mounted on one of the grills of the vehicle air-conditioning equipment, so that the circulation of air over the wick is a function not only of the degree of opening of the container thereof, but also of the speed of the fan of the vehicle which impels the air toward the aforementioned diffuser grill.

In a more specific way in the European patent mentioned above, the control of air flow is regulated by means of a cap which covers the wick and which is moveable axially with respect to the cap with the collaboration of a rack and a small pinion. The pinion is provided with an externally operated control.

For its part and for the fastening of the diffuser to the diffuser grill of the vehicle, it has been foreseen that the casing of the diffuser incorporates a clip with four arms in its rear face so that the clip is able to grasp a slat of the diffuser grill of the vehicle. The clip permits the diffuser to be mounted both in a horizontal position and vertically, the diffuser maintaining a correct working position, in either case.

SUMMARY OF THE INVENTION

The present invention provides a diffuser of air-freshening or aromatic products, adapted to be used inside a motor vehicle, and provided with a fastener for fastening the diffuser to a diffuser grill of the air conditioning system of the vehicle and also including an adjustment by which a user may adjust the flow of air that passes through the diffuser. As a consequence, the quantity of air-freshening product delivered to the atmosphere per unit of time is adjustable.

The invention achieves optimum functional benefits from the diffuser, as just mentioned, while also being structurally simple.

BRIEF DESCRIPTION OF THE DRAWINGS

Embodiments of the invention are disclosed in greater detail hereinbelow, as shown in the attached drawings and described in the accompanying text.

DETAILED DESCRIPTION OF THE PREFERRED EMBODIMENTS

Figure 1:
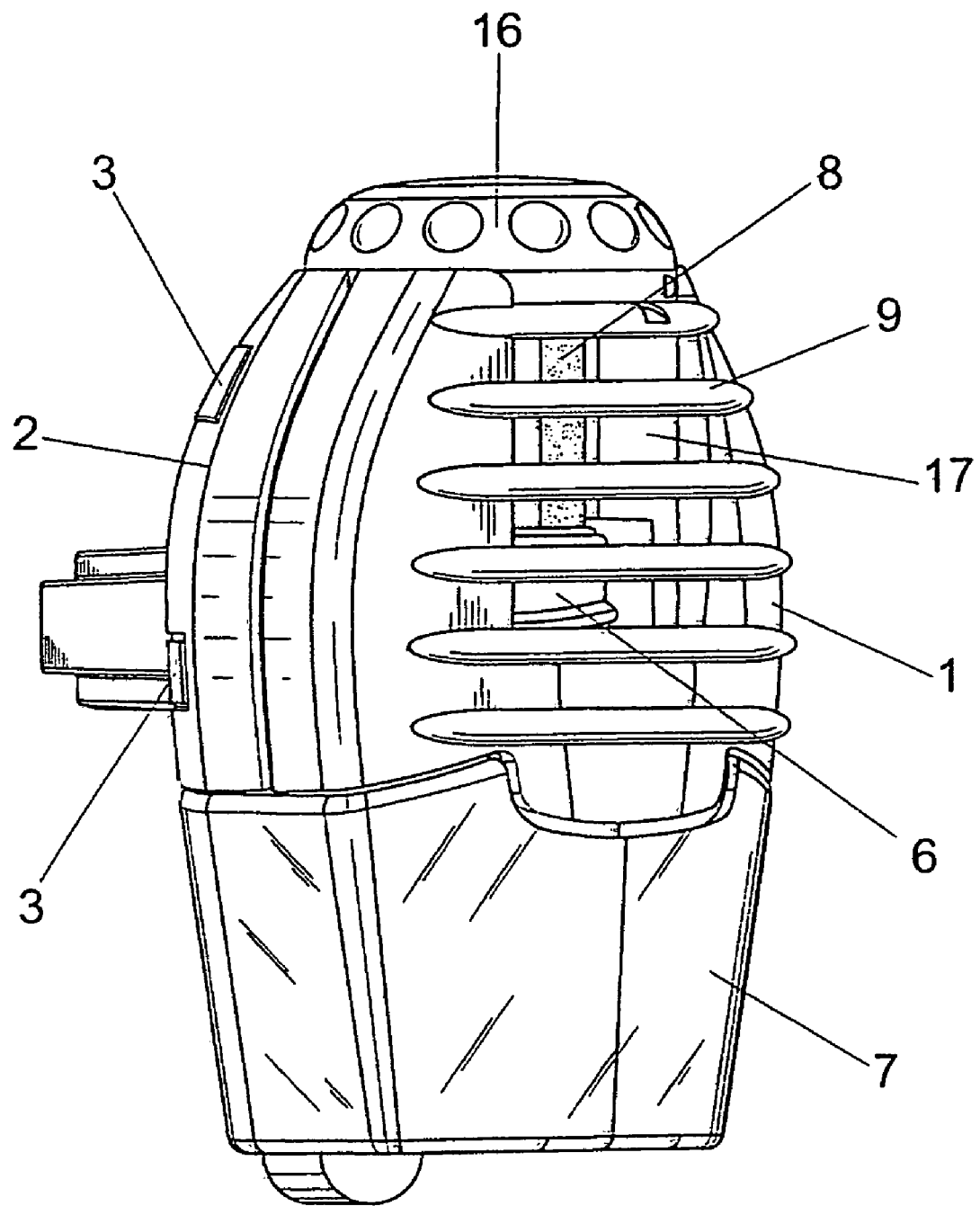
FIG. 1 is a front corner view in perspective of a diffuser for air-freshening products for use in a vehicle in accordance with the object of the present invention.
Figure 2:
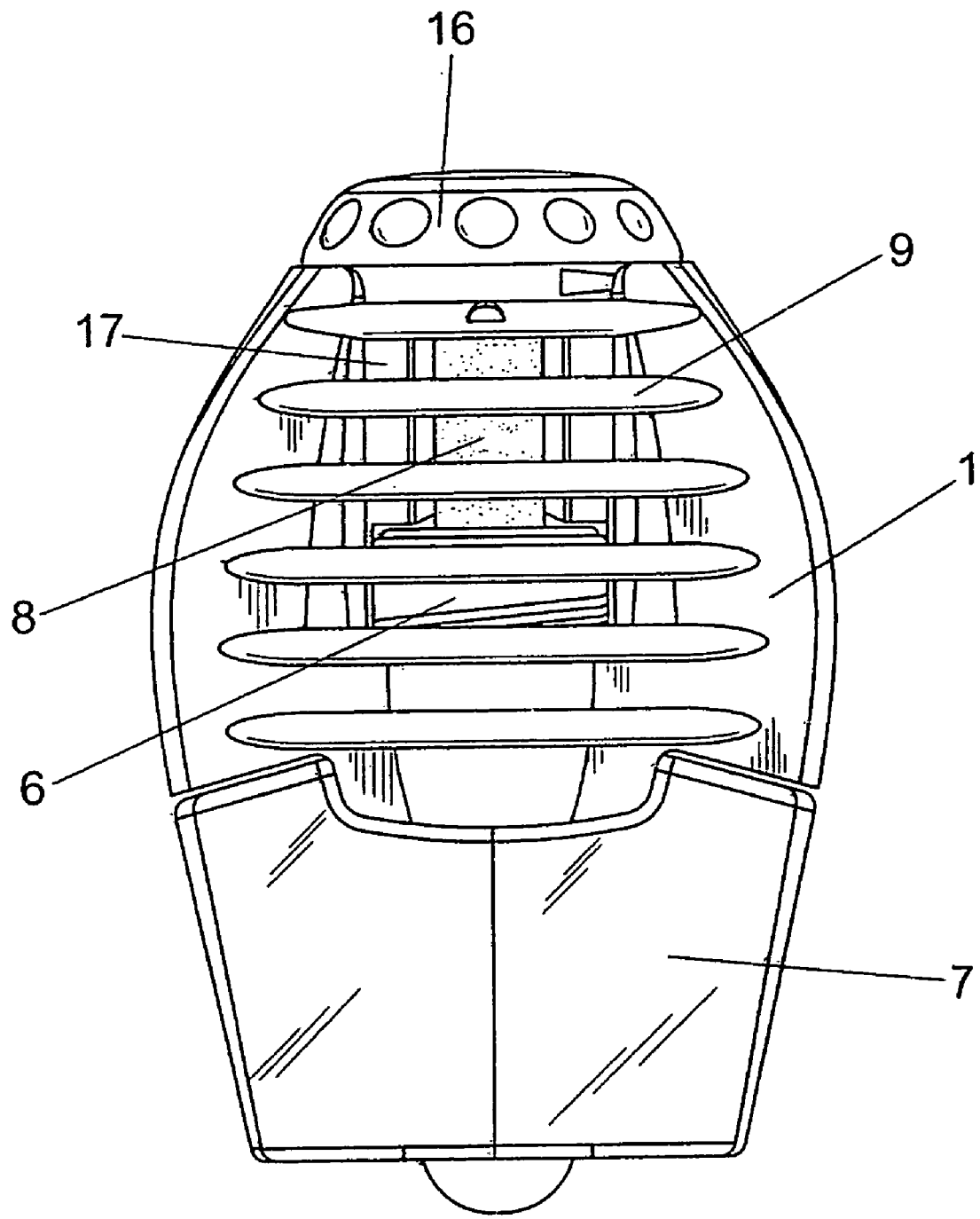
FIG. 2 is a view in front elevation of the diffuser of FIG. 1.

The diffuser of preferred embodiments of the present invention provides improved regulation of the emission capacity of the air-freshening product per unit of time, in particular, with the present air freshener diffuser fastened to the diffuser, or vent, grill of the air-conditioning system of the vehicle. In a particular embodiment, the diffuser has two half-casings, a front casing and a rear casing, capable of coupling to each other by matched engagement. Each of the casings are provided with a section having air openings intermediate of the casing body for the passage of air therethrough, and both casings define as a whole, when in an assembled position, a cylindrical lower neck in which is tightly coupled the neck of a reservoir container for the air-freshening product so that a wick for the air freshener product is facing the section with the air openings.

A control for varying the air flow through the casing is provided, the control having an air flow regulating portion within the casing and a knob or other projection extending from the casing for operation by a user to vary the air flow. In one embodiment, a second neck is provided within the casing above, and coaxial with, the lower neck and coaxial with the wick that extends into the reservoir. This upper neck holds a plug element. The upper neck includes a peripheral and internal rib which runs in a groove of the plug element, the plug element in turn projecting upwardly from the casing to provide an upper manually operated knob that may be operated by the user. At the bottom of the plug is provided two skirts, which are in diametrical opposition to one another and which are capable of blocking the sections with the air openings in the half-casings to a greater or lesser extent as the plug is rotated. In one embodiment, the possibility is provided that one of the skirts is shorter than the other so that the length of this shorter skirt is approximately one third the length of the other, longer skirt. This ensures that the casing sections with the air openings are offset with respect to the intermediate portion of the wick in the intermediate opening position, forcing the air to follow a longer path through the diffuser, specifically a winding path or path encircling the wick, which improves the evaporation conditions.

The air flow control is provided with a structure to define end positions of the opening movement, one position corresponding to the fully open position and the other position corresponding to the closed position. In the embodiment with the plug element, the plug is provided with a widened section of the groove that is mentioned above, the widened portion of the groove extending around approximately a quarter of the plug diameter. A lug is provided extending from one of the two half-casings into the widened portion of the groove to define the limits of the fully opened and fully closed end positions of the plug. This plug is operated manually from above and it can incorporate indicators that facilitate viewing the degree of opening of the evaporator.

Likewise, the sections of the casings that have the air openings are in one embodiment formed as grills, at least in the front half-casing, so that the position of the air flow control, in one embodiment the plug element, may be viewed through the grill. The displacement of the plug element from the open or closed positions may be viewed readily to determine the degree of opening of the air flow passage to the wick without it being necessary for the user to see any other graphic printed on the plug.

In accordance with another characteristic of an embodiment of the invention, the rear half-casing incorporates, as a means of fastening to the diffuser grill of the air-conditioning equipment of the vehicle, a clip provided with two arms, which represents a significant simplification in the clip compared to the prior art device with a four armed clip, without prejudice to the features thereof. It is preferred that the clip is mounted to be removable from and attachable to the rear half-casing. As a consequence, it is possible to mount the diffuser at either a horizontal or a vertical position, according to the necessities of each case. In addition to simplifying the structure of the diffuser, the absence in the clip of two inoperative arms compared to the prior art device with four arms also eliminates the problem of double clips, wherein it is necessary to eliminate two of the arms by breaking to prevent them from causing an obstruction by resting on the slat or partition of the diffuser grill.

Figure 3:
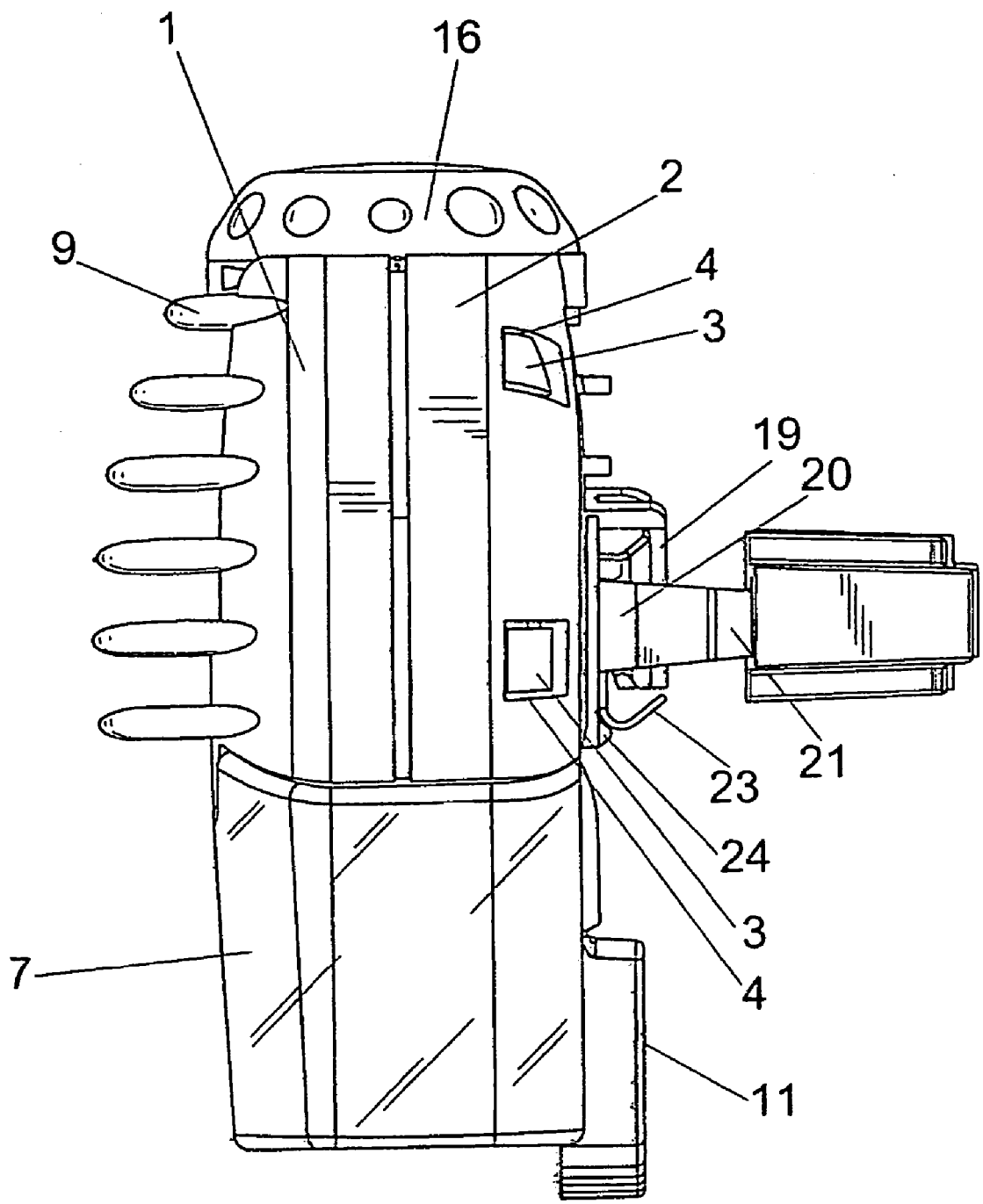
FIG. 3 is a profile view of the present diffuser.
Figure 4:
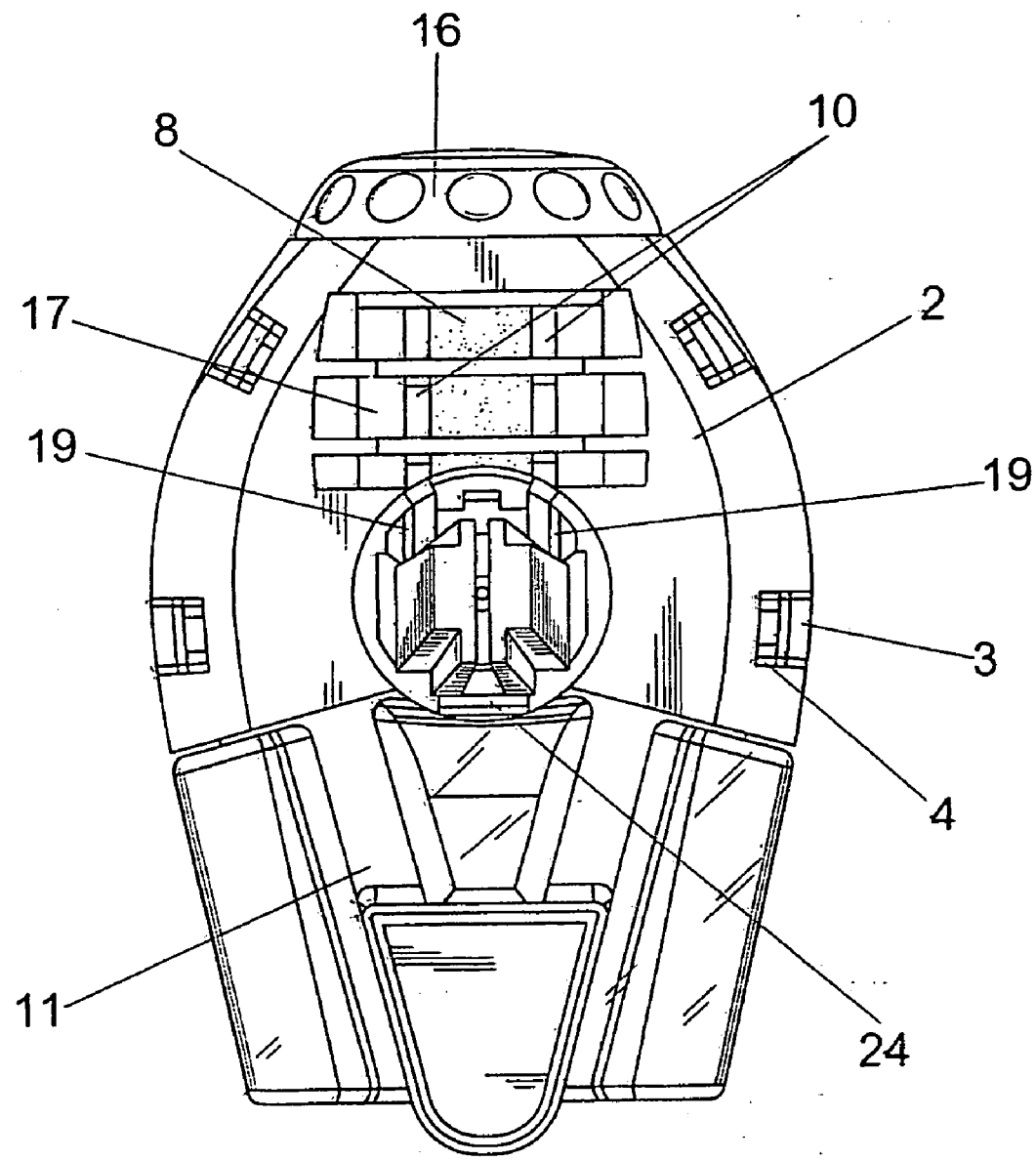
FIG. 4 is a view in rear elevation in which two skirts of the plug have the same length.
Figure 5:
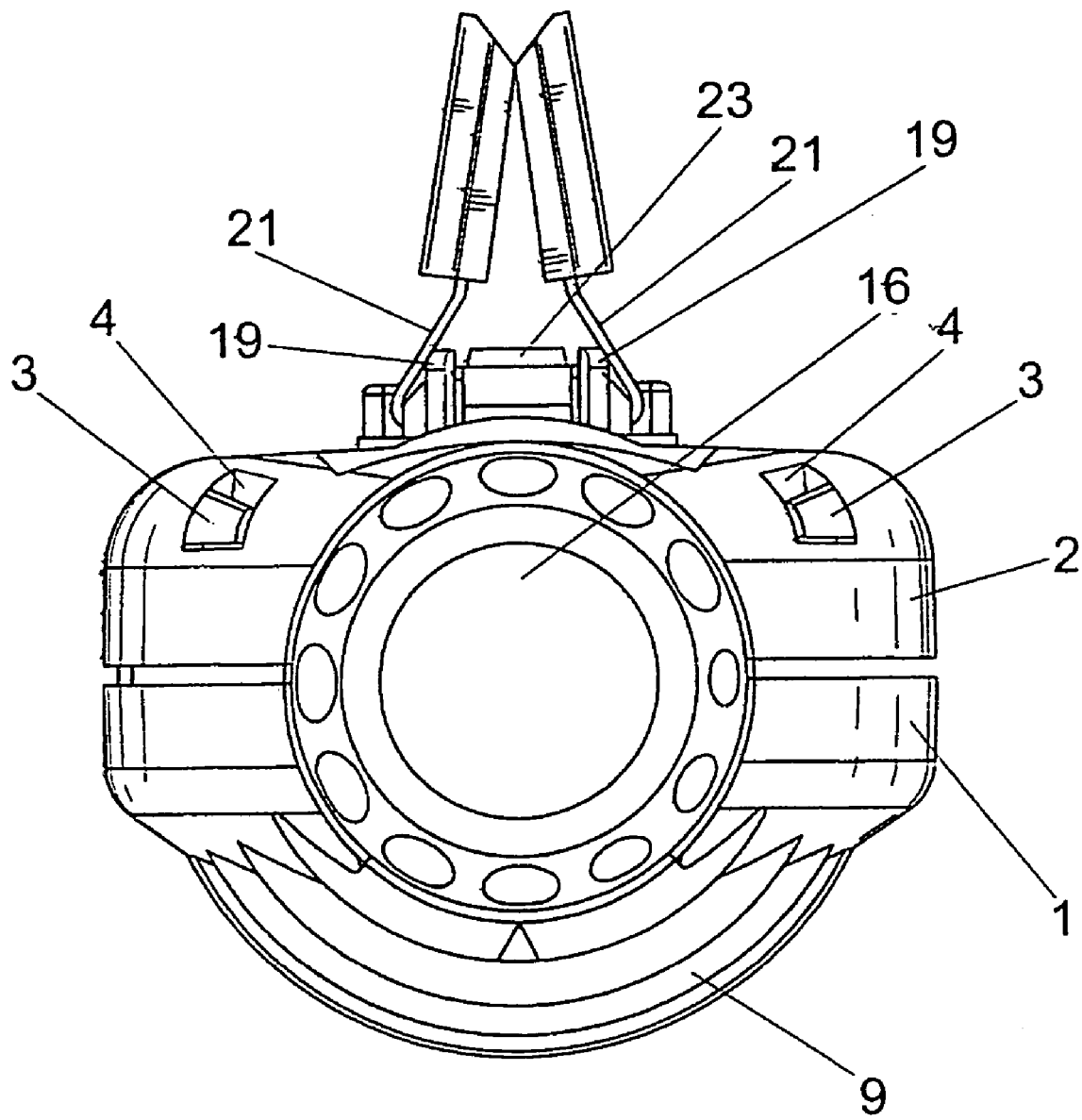
FIG. 5 is a top plan view of the diffuser.
Figure 6:
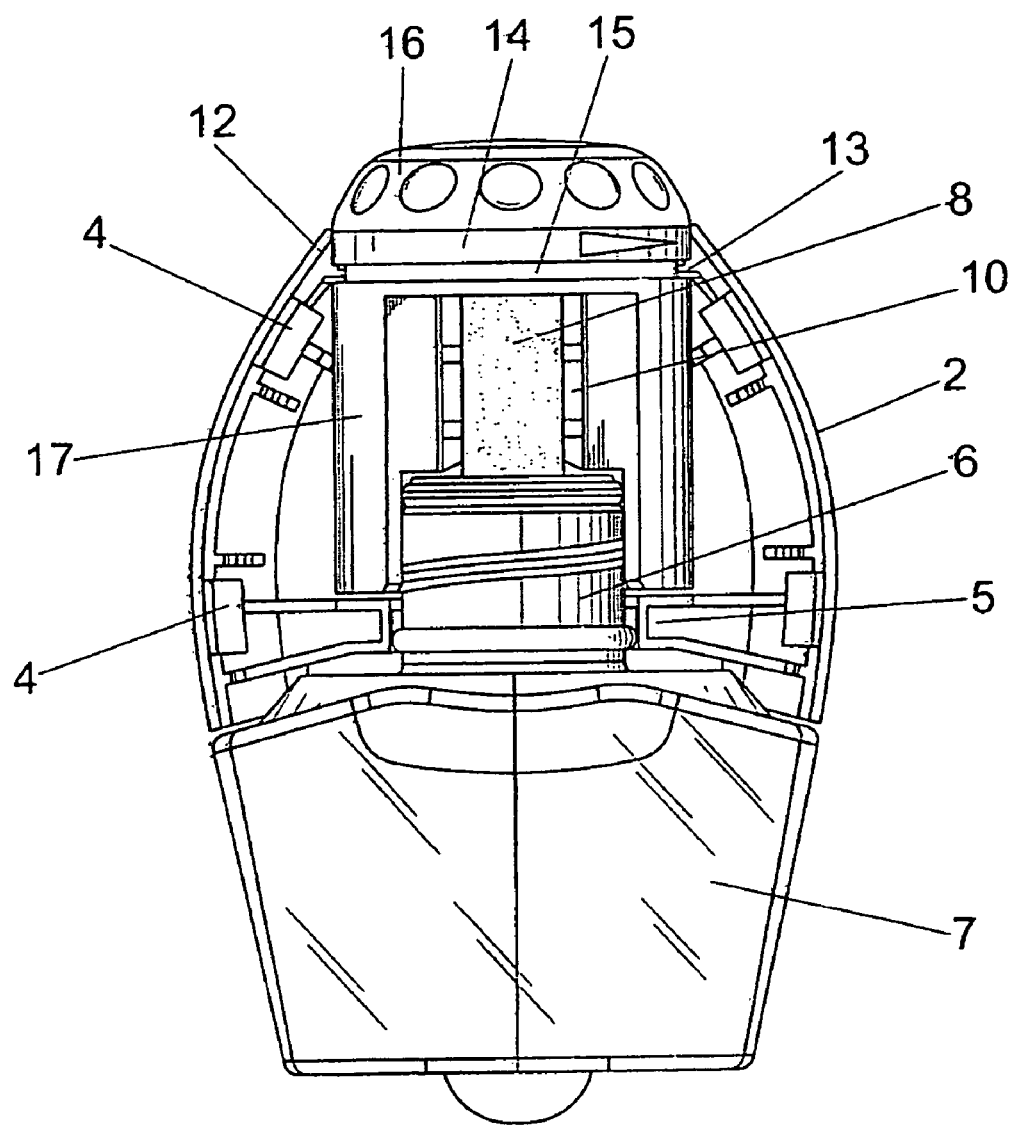
FIGS. 6 and 7 are two views in front elevation of the diffuser, with its front half-casing removed, FIG. 6 showing the casing in the fully open position and FIG. 7 showing the casing fully closed.

With reference to the figures, the diffuser in FIG. 1 of the illustrated embodiment has two half-casings, one front casing 1 and one rear casing 2. The casings 1 and 2 are formed by injection molding using a plastic material. The casings 1 and 2 are fastened to one another by some fastening means, which may include various fasteners, welds, snaps, etc. In the illustrated embodiment as shown in FIG. 3, the front casing 1 has four elastically deformable tabs 3 that extend into respective openings 4 by which the front casing is coupled by matched engagement to the rear half-casing 2. The connection of the two half-casings 1 and 2 forms a lower cylindrical neck 5 inside the diffuser body, as shown in FIG. 6. The lower neck is coupled to a neck 6 of a reservoir container 7 for an air-freshening product. A wick 8 of a wicking material projects from the neck 6 and is housed axially inside the casings 1 and 2. The wick 8 absorbs the air-freshening product so that it is carried by air currents which traverse the casing, such as through two slotted sections or grills 9 and 10, as shown in FIGS. 3 and 4, that are present in the front half-casing 1 and rear half-casing 2, respectively. The grill shaped openings 9 and 10 are provided in the preferred embodiment, but it is within the scope of this invention that other shapes and arrangements of air flow openings may be provided. The casings 1 and 2 are centered and facing each other. The reservoir 7 is stabilized inside the diffuser with the aid of a retention arm 11 that is a lower continuation of the rear half-casing 2.

As an air flow control in the preferred embodiment, the half-casings 1 and 2 define a second neck 12, as shown in FIG. 6, at the level of the upper end, in which a peripheral rib 13 is provided for coupling to a plug 14 so that the plug 14 is able to rotate. The plug 14 is provided with a groove 15 for coupling with the rib 13. The outside of the plug 14 has an outwardly projecting knob 16 (which here extends upwardly with respect to the FIG. 6) for manual operation, i.e. rotation, of the plug 14. At the bottom of the plug 14 and internally of the casings 1 and 2 are provided a pair of skirts 17. The skirts 17 are offset from the grills 9 and 10. The rotation of the knob 16 in an imaginary cylindrical plane causes the skirts 17 to be rotated between an open position, as shown by the position illustrated in FIG. 6, and a position closing the grills completely, just as occurs in the position shown in FIG. 7, or the knob 16 may be rotated to any intermediate position.

It is possible that other shapes and arrangements of air flow controls may be provided as well. The preferred air flow control has a projection or knob extending from the casing to permit the user to adjust the air flow through the device.

Figure 9:
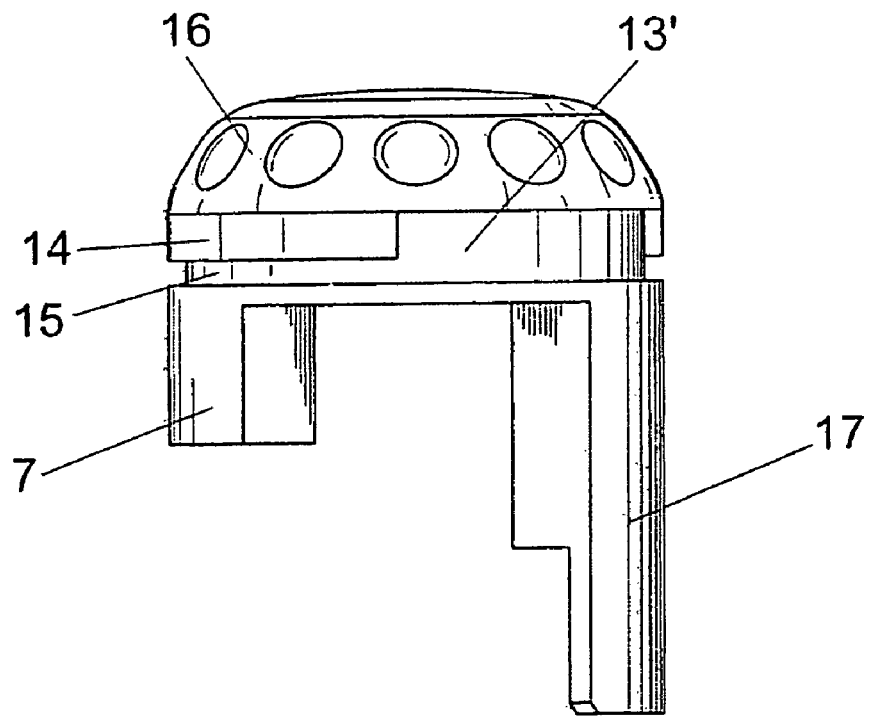
FIG. 9 is a detailed front elevation of the rear half-casing in which the two skirts have mutually different lengths.

It is possible in one embodiment for one of the skirts 17 extending from the plug element to be cut or formed shorter, so that the length of the shorter skirt 17' is approximately one third the length of the other, longer skirt 17, as shown in FIG. 9. This second embodiment of the skirts is capable of assuming any rotated position with respect to the slotted sections or grills 9 and 10.

Figure 7:
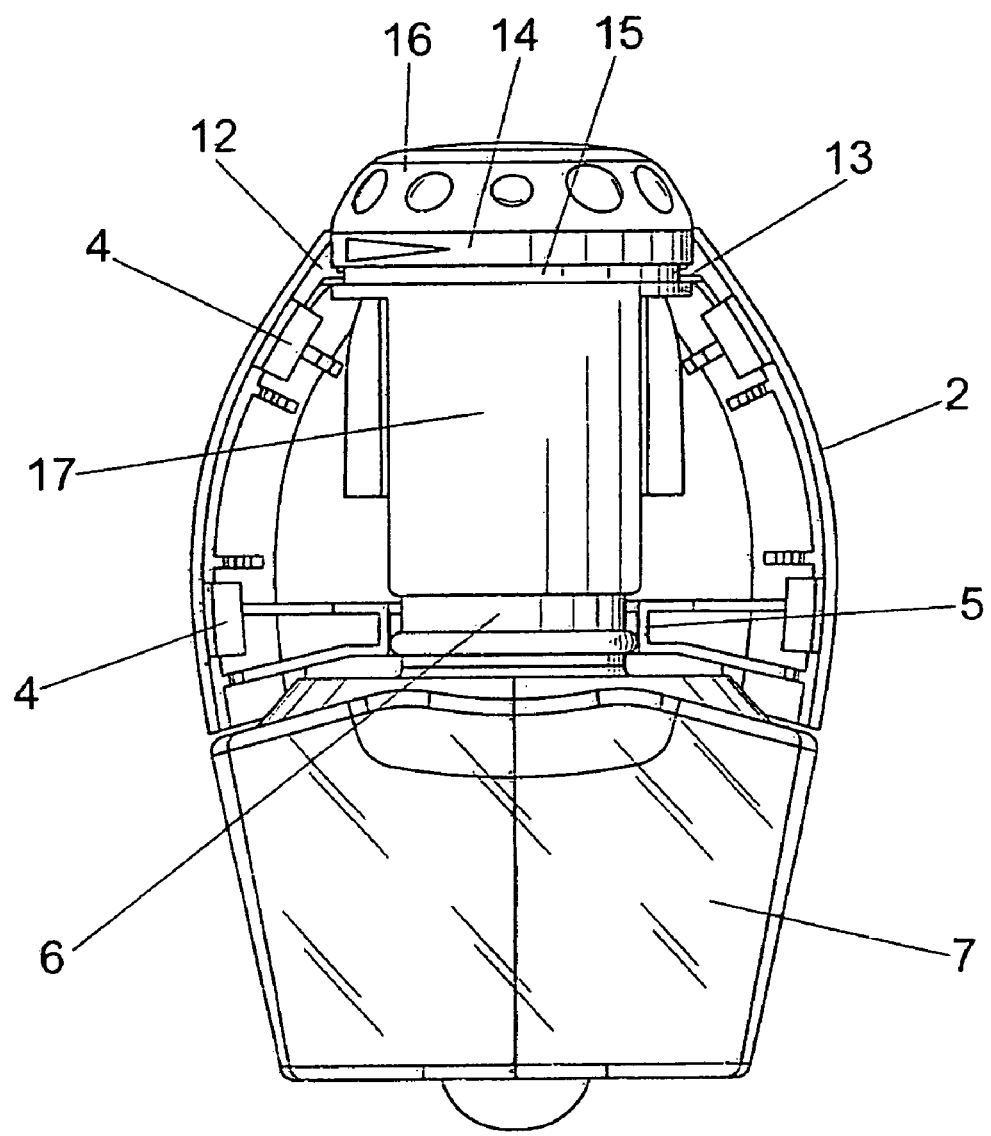
Figure 8:
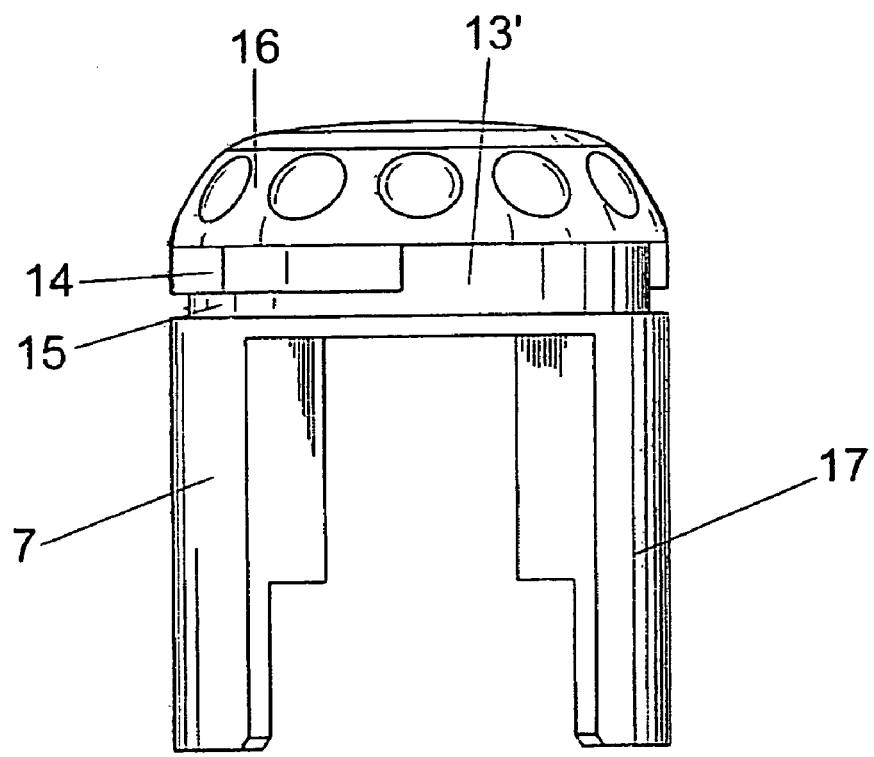
FIG. 8 is a detailed side elevation of the plug in which the two skirts having the same length.
Figure 11:
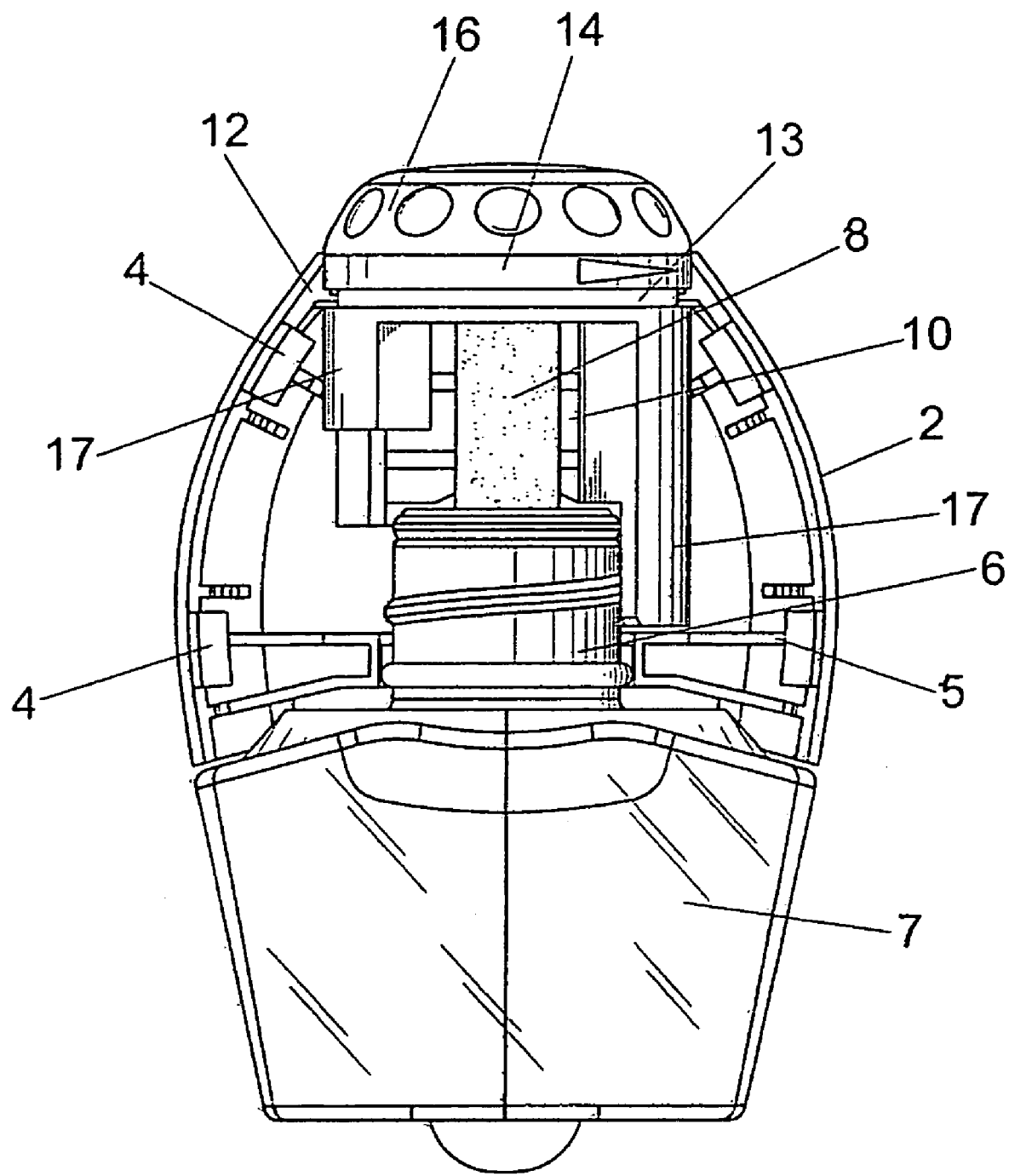
FIG. 11 is a front elevational view of the diffuser, without its front half-casing in a full aperture position in which the skirts have a different length.
Figure 12:
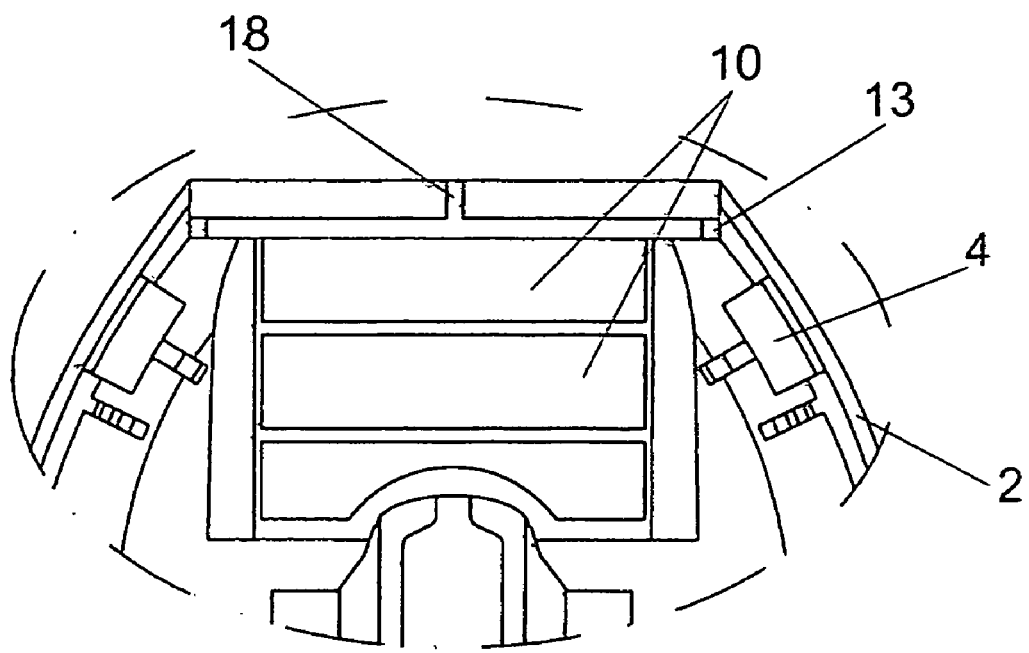
FIG. 12 is a front elevational view of the rear half-casing.

The opening and closing limiting positions of the diffuser, more specifically the air flow limiting positions of the plug 14, are defined by a widened portion 13' (as shown in FIGS. 8 and 9) of the groove 13 (as shown in FIG. 7), in which runs a lug 18 (as shown in FIG. 12) projecting inwardly from the neck 12 (as shown in FIG. 11) of the rear half-casing 2. The extent to which the wick 8 is exposed in any position of the plug 14 is directly visible for the user through the front grill 9.

The form of the front grill 9 allows viewing of the air regulator plug element 14 so that the degree of evaporation and diffusion of the device can be quickly determined by viewing the positions of the skirts 17.

Figure 10:
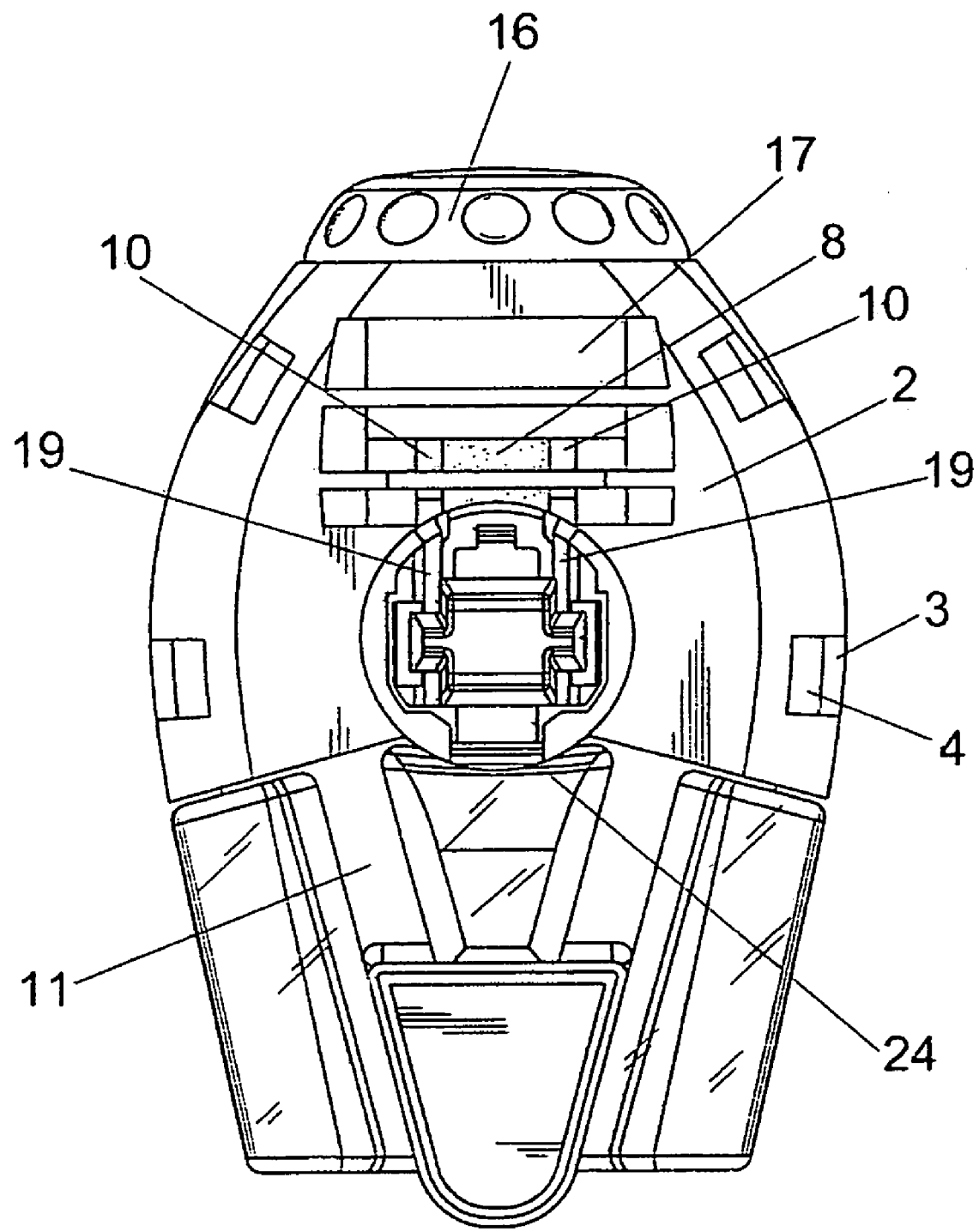
FIG. 10 is a detailed rear elevation showing the two skirts with different lengths.

As an addition to the structure described, the rear half-casing 2 incorporates, under the slotted section or grill 10, a fastener for a clip to permit the diffuser to be clipped to the air conditioner or vent openings of a vehicle. In the illustrated embodiment, the fastener for the clip is a fork element 19 having two arms that extend backward and downward at an elbow, as may be especially observed in the detail of FIG. 10. The fork element 19 engages with a clip that holds the diffuser in place.

Figure 14:
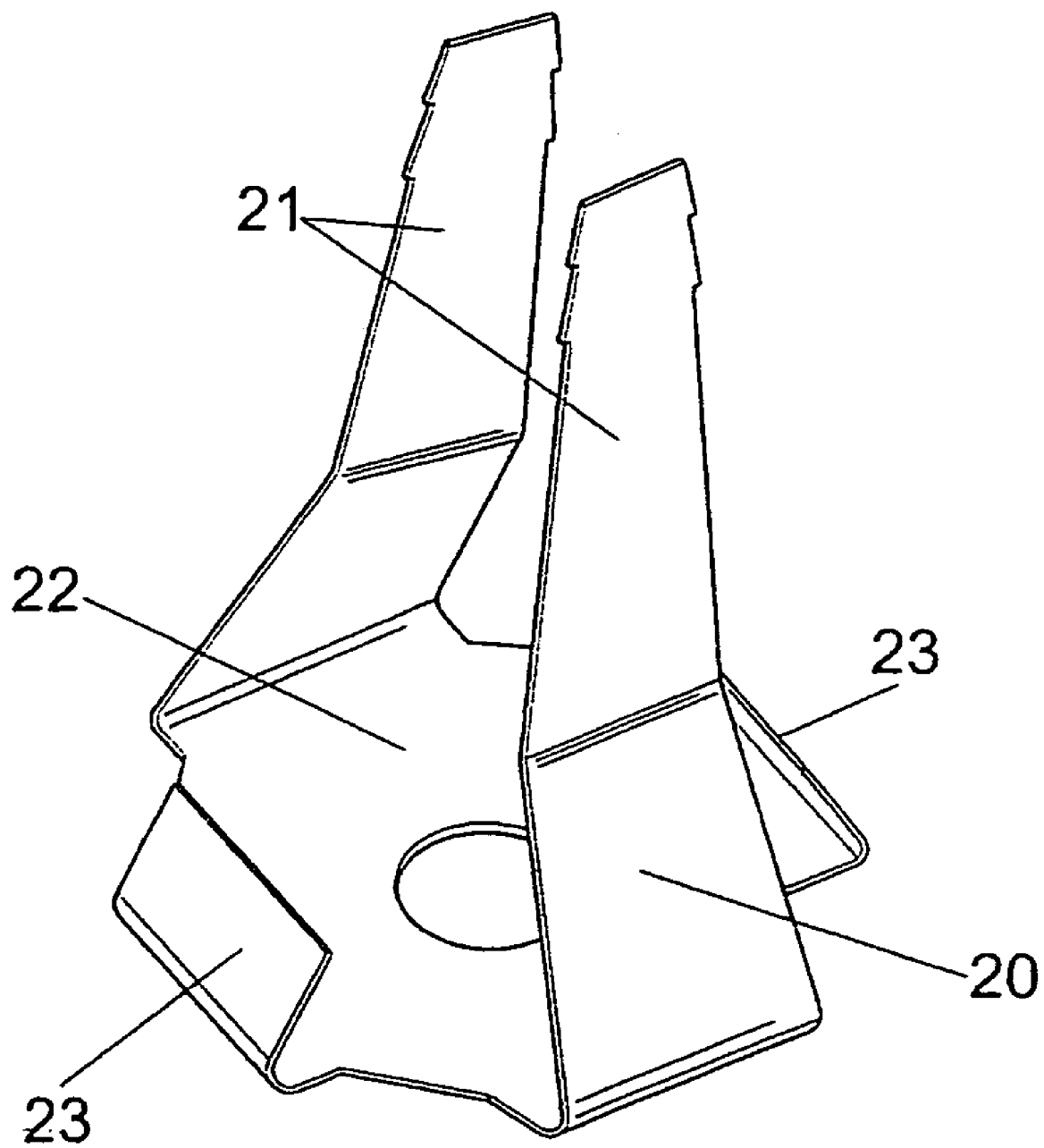
FIG. 14 is a detailed perspective view of the clip of FIG. 13.

As shown in FIG. 14, one embodiment of a clip is provided, which permits the diffuser to be fastened to the air conditioner grill of a vehicle. The clip is formed of metal and has side extensions or webs 20 that can be positioned between the arms of the forked element 19. The metallic side extension or webs 20 of the clip are each covered with a jacket or coating 21 of plastic material. The side webs 20 in particular are elastically deformable and extend from opposite sides of a base 22, converging toward one another to permit the side webs to grasp slats of the air conditioner vents of the vehicle. Two other, shorter arms 23 extend from the base as well in the illustrated embodiment. These shorter arms are offset by 90° with respect to the longer side arms or webs 20. Like the longer arms 20, the shorter arms 23 converge toward one another but are considerably shorter. Other shapes of arms may be provided as well, so long as the clip is fastenable into the fastener portion on the back of the diffuser.

Figure 13:
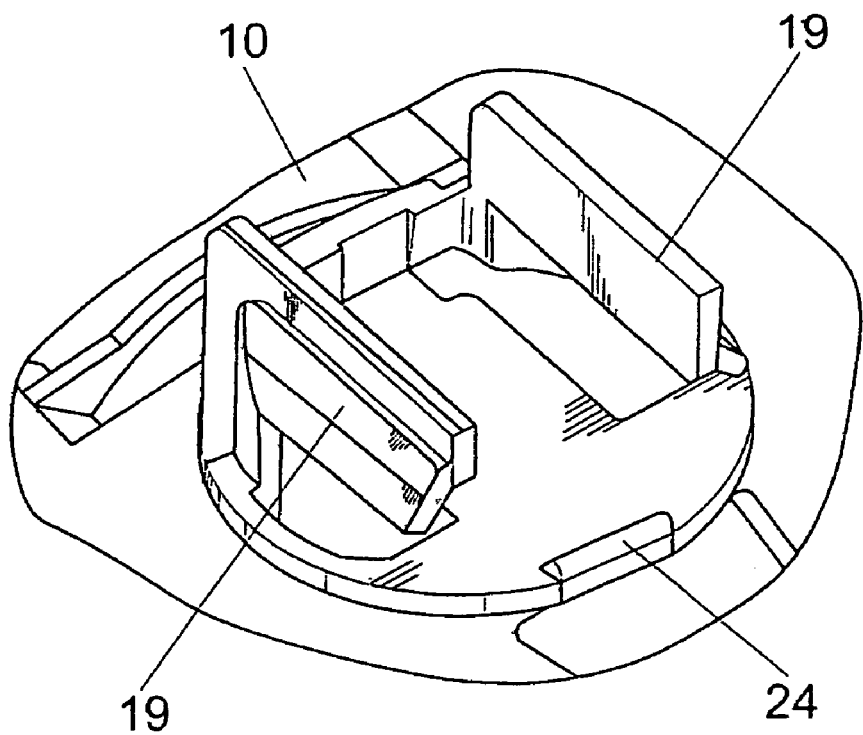
FIG. 13 is a detailed perspective view of the rear half-casing, from its rear or external face and at a level of a means of fastening of the clip.

The clip can be assembled to the diffuser casing by coupling to the fork element 19 in a matched engagement and by a slight elastic deformation of the fork element. The clip may be fastened in either of two different positions which are rotated by 90° with respect to one another so that the clip can be positioned in the horizontal direction and the vertical direction according to the specific needs of each case. Specifically, the clip will fasten the diffuser to a vehicle air conditioner vent slat that is oriented vertically or horizontally so that the device may be used in a wide variety of vehicles without limitation to the orientation of the air conditioner vent slats. The base 22 stabilizes the clip in its selected working position against the rear casing, and a small rib 24, as shown in FIG. 13, is provided on an outside wall of the rear half-casing 2. The rib 24 faces the open end of the forked element 19 so that the base 22 of the clip is insertable into the forked element 19 by pressing the rib 24 and base 22 passed each other, with a slight elastic deformation, in an assembled position.

The clip of FIG. 14 is pressed into a grill opening of the air conditioner vent of a vehicle so secure the clip into place. In particular, the coated ends 21 of the arms 20 fit into a grill slot and the tapered edges bear against the inside surfaces of the grill slot so that the base 22 extends out from the air conditioner grill. The diffuser of the present invention is thereafter clipped into place on the clip and can be clipped in either a horizontal orientation or a vertical orientation.

The references to a vehicle air conditioner or air ventilation system vent or grill include without limitation an air cooling system, heated air circulating system, fresh air circulating system, filtered air flow system, or forced air system. The air leaving the vent or grill may pass through the present diffuser, picking put vapors from the air freshener product, and flow into the interior of the vehicle. The air flow is controllable by the fan of the air conditioner or vent system and by user adjustment of the control on the present diffuser. The quantity of air freshening product is thus controllable.

Although other modifications and changes may be suggested by those skilled in the art, it is the intention of the inventors to embody within the patent warranted hereon all changes and modifications as reasonably and properly come within the scope of their contribution to the art.

The invention claimed is:

1. A diffuser for an air-freshening product for a vehicle, comprising:
 a casing having openings for passage of air therethrough, said openings being selectively closable to a greater or lesser extent;
 a reservoir container for the air-freshening product, said reservoir container being removably coupled to said casing;
 a wick extending from said reservoir container to enable evaporation of the air-freshening product, said wick being housed inside said casing;
 a fastener to fasten said casing to a diffuser grill of an air ventilation system of a vehicle;
 said casing defining two cylindrical neck openings, said two neck openings being coaxial with one another and being open to an exterior of said casing, said two cylindrical neck openings including a lower neck opening and an upper neck opening, said lower neck opening receiving said reservoir container when said reservoir container is coupled to said casing;
 a plug element rotatably positioned in said upper neck opening, said plug element having an operating knob at a position exterior to said casing, said plug element having first and second skirt portions extending from a body of said plug element at an end opposite said operating knob, said skirt portions being inside said casing, said first and second skirt portions being spaced from one another and being diametrically opposed to one another on said body of said plug element, rotation of said plug element selectively blocking and alternatively unblocking said openings in said casing by moving at least one of said first and second skirt portions to block said openings and alternatively to unblock said openings of said casing;
 said wick having a first end inside said reservoir container, and a second end located between said two neck openings of said casing for passage of air.

2. A diffuser of air-freshening products for vehicles according to claim 1, wherein said plug defines a groove extending along at least a portion of a periphery of said plug, and
 wherein said casing includes two half casings, said two half casings including a front casing and a rear casing, said two half casings including tabs and openings to receive said tabs to fasten said front casing and said rear casing to one another in matched engagement;
 said upper and lower neck openings being defined by fastening of said front casing and said rear casing;
 said upper neck opening including an internal peripheral rib extending into said groove in said plug element to permit rotation of said plug element while restricting axial movement, said groove defining a widened portion and a lug extending into said widened portion to restrict rotational motion of said plug element to define end positions for opening and closing of said plug element.

3. A diffuser of air-freshening products for vehicles as claimed in claim 2, wherein at least one of said first and second skirt portions are visible through said openings in said front casing to permit viewing of a position of said at least one of said skirt portions relative to fully opened, partially opened and closed positions.

4. A diffuser of air-freshening products for vehicles, as claimed in claim 2, wherein said first and second skirts are of mutually different lengths.

5. A diffuser of air-freshening products for vehicles, as claimed in claim 4, wherein a longer one of said two skirts is approximately three times longer than a shorter one of said two skirts.

6. A diffuser of air-freshening products for vehicles, comprising:
 a casing having openings for passage of air therethrough, said openings being selectively closable to a greater or lesser extent;
 a reservoir container for the air-freshening product, said reservoir container being removably coupled to said casing;
 a wick extending from said reservoir container to enable evaporation of the air-freshening product, said wick being housed inside said casing;
 a fastener to fasten said casing to a diffuser grill of an air ventilation system of a vehicle;
 said casing defining two cylindrical neck openings, said two neck openings being coaxial with one another and being open to an exterior of said casing, said two cylindrical neck openings including a lower neck opening and an upper neck opening, said lower neck opening receiving said reservoir container when said reservoir container is coupled to said casing;

a plug element rotatably positioned in said upper neck opening, said plug element having an operating knob at a position exterior to said casing, said plug element having first and second skirt portions extending from a body of said plug element at an end opposite said operating knob, said skirt portions being inside said casing, said first and second skirt portions being spaced from one another and being diametrically opposed to one another on said body of said plug element, rotation of said plug element selectively blocking and alternatively unblocking said openings in said casing by moving at least one of said first and second skirt portions to block said openings and alternatively to unblock said openings of said casing wherein said plug defines a groove extending along at least a portion of a periphery of said plug, and wherein said casing includes two half casings, said two half casings including a front casing and a rear casing, said two half casings including tabs and openings to receive said tabs to fasten said front casing and said rear casing to one another in matched engagement;

said upper and lower neck openings being defined by fastening of said front casing and said rear casing;

said upper neck opening including an internal peripheral rib extending into said groove in said plug element to permit rotation of said plug element while restricting axial movement, said groove defining a widened portion and a lug extending into said widened portion to restrict rotational motion of said plug element to define end positions for opening and closing of said plug element;

a forked element on said rear casing below a openings in said rear casing a clip selectively fastenable in said forked element, said clip including two arms disposed in opposition to one another, said two extended arms including coatings of an elastromeric material, said clip having a substantially flat base, two further arms extending from said base at positions offset by approximately 90° with respect to said two extended arms, said two further arms being substantially shorter than said two extended arms, said two extended arms converging toward one another, said two further arms extending toward one another, said forked element being fastenable in engagement with said two extended arms in a first position and alternately being fastenable in engagement with said two further arms by press fitting in a second position, said first position and being rotated approximately 90 degrees from said second position; and a projection on an outside wall of said rear casing engaging said clip as said clip is in an engaged position in said forked element.

7. A diffuser for an air-freshening product for a vehicle, comprising:

a casing having openings for passage of air through said openings;

a reservoir container for the air-freshening product, said reservoir container being removably coupled to said casing;

a wick extending from said reservoir container to enable evaporation of the air-freshening product, said wick being housed inside said casing;

a fastener to fasten said casing to a diffuser grill of an air ventilation system of a vehicle;

said casing defining a neck opening into which said reservoir container is received to position said wick within said casing, said reservoir container being selectively removable from said neck opening to remove said reservoir from said casing for replacement or refill; and an air flow control element fastened in said casing and having a knob extending from said casing, said air flow control element being movable between positions blocking air flow through said casing to a greater or lesser extent, said knob being operable by a user to selectively position said air flow control element at said positions, the air flow control element including first and second skirt portions extending from said knob at diametrically opposed locations, said first and second skirt portions being spaced from one another and defining a gap therebetween; and said wick having a first end in said reservoir container and a second end in said gap between said first and second skirt portions.

8. A diffuser of air-freshening products for vehicles according to claim 7, wherein said casing includes two half casings fastened to one another, said air flow control element being secured in said casing by fastening of said two half casings together.

9. A diffuser as claimed in claim 7, wherein said air flow control element and said casing are in cooperative engagement to define a maximum air flow position and a minimum air flow position of said air flow control element, said air flow control element being selectively positionable in at least one intermediate position between said maximum air flow position and said minimum air flow position.

10. A diffuser of air-freshening products for vehicles as claimed in claim 9, wherein said air flow control element is visible through said openings in said casing to permit viewing of a position of said air flow control element.

11. A diffuser as claimed in claim 7, wherein said knob extending from said casing is viewable to indicate an extent of opening of air flow through said casing.

12. A diffuser for an air-freshening product for a vehicle, comprising:

a casing having openings for passage of air through said openings;

a reservoir container for the air-freshening product, said reservoir container being removably coupled to said casing;

a wick extending from said reservoir container to enable evaporation of the air-freshening product, said wick being housed inside said casing;

a fastener to fasten said casing to a diffuser grill of an air ventilation system of a vehicle;

said casing defining a neck opening into which said reservoir container is received to position said wick within said casing, said reservoir container being selectively removable from said neck opening to remove said reservoir from said casing for replacement or refill; and an air flow control element fastened in said casing and having a knob extending from said casing, said air flow control element being movable between positions blocking air flow through said casing to a greater or lesser extent, said knob being operable by a user to selectively position said air flow control element at said positions, the air flow control element including first and second skirt portions extending from said knob at diametrically opposed locations, said first and second skirt portions being spaced from one another and defining a gap therebetween wherein said air flow control element and said casing are in cooperative engagement to define a maximum air flow position and a minimum air flow position of said air flow control element, said air flow control element being selectively positionable in at least one intermediate position between said maximum air flow position and said minimum air flow position;

wherein said fastener includes a clip element having a base and first and second flexible arms extending from said base and positioned to engage an air conditioner grill of a vehicle, said casing having a fastener portion on said casing, said base being selectively securable into said fastener portion to secure said clip to said housing.

13. A diffuser as claimed in claim 12, wherein said fastener portion and said base are shaped to provide securing of said clip to said casing in at least two different positions oriented approximately 90 degrees from one another.

14. A diffuser as claimed in claim 13, wherein said fastener portion on said case includes first and second arm portions directed mutually inwardly and disposed substantially parallel to one another to engage opposite sides of said base of said clip.

15. A diffuser as claimed in claim 14, further comprising:
a plastic coating on said first and second flexible arms of said clip.

* * * * *